United States Patent [19]

Chilson et al.

[11] Patent Number: 4,699,147
[45] Date of Patent: Oct. 13, 1987

[54] INTRAVENTRICULAR MULTIELECTRODE CARDIAL MAPPING PROBE AND METHOD FOR USING SAME

[75] Inventors: Donald A. Chilson, Spokane, Wash.; Kevin W. Smith, Miami, Fla.

[73] Assignee: Cordis Corporation, Miami, Fla.

[21] Appl. No.: 779,948

[22] Filed: Sep. 25, 1985

[51] Int. Cl.$^4$ ............................................... A61B 5/04
[52] U.S. Cl. .................................... 128/642; 128/786
[58] Field of Search ................ 128/642, 783, 784, 786

[56]      References Cited

U.S. PATENT DOCUMENTS

| | | | |
|---|---|---|---|
| 3,326,207 | 6/1967 | Egan | 128/642 |
| 3,825,015 | 7/1974 | Berkovits | 128/404 |
| 3,865,118 | 2/1975 | Bures | 128/419 P |
| 3,903,897 | 9/1975 | Woollons et al. | 128/419 PG |
| 3,995,623 | 12/1976 | Blake et al. | 128/2.06 E |
| 4,172,451 | 10/1979 | Kline | 128/642 |
| 4,281,660 | 8/1981 | Fujiwara | 128/642 |
| 4,289,138 | 9/1981 | Halvorson | 128/642 |
| 4,522,212 | 6/1985 | Gelinas et al. | 128/642 |

FOREIGN PATENT DOCUMENTS

| | | | |
|---|---|---|---|
| 9732 | 4/1980 | European Pat. Off. | 128/785 |
| 3203300 | 8/1982 | Fed. Rep. of Germany | 128/642 |

OTHER PUBLICATIONS

Berens et al., "The American Journal of Cardiology", vol. 34, Sep. 1974, pp. 325–332.

*Primary Examiner*—William E. Kamm
*Attorney, Agent, or Firm*—Henry W. Collins; Thomas R. Vigil

[57]      ABSTRACT

The intraventricular multielectrode cardiac mapping probe comprises a catheter having an open proximal end and an open distal end and four elongate wire assemblies received in the catheter and having a distal end portion, and a proximal end portion extending from the catheter proximal open end. Each wire assembly comprises a tubing, six insulated wire conductors received in the tubing, and a central core wire which is stiff but yet flexible and which is received in the tubing and extends substantially the length thereof. A proximal connector is mounted on each tubing. The distal end portion of each wire assembly has six spaced apart sleeve electrodes thereon connected to respective ones of the wire conductors. The portion of each core wire in the distal end portion of one of the wire assemblies can be caused to assume a desired configuration after the wire assembly distal end portions are moved from a retracted position within the catheter to a position where the distal end portions are extended from the catheter and where the core wires can be caused to assume the desired configuration to form an elliptical envelope. The catheter is adapted to be inserted into an artery or vein to place the distal end opening thereof in a heart chamber from which the distal end portions of the wire assemblies can be extended to create the elliptical envelope and then can be incrementally rotated while electrical potentials are measured and recorded at different points along the surface of an endocardial wall of a heart chamber (e.g., ventricle) that come into contact with the sleeve electrodes.

25 Claims, 6 Drawing Figures

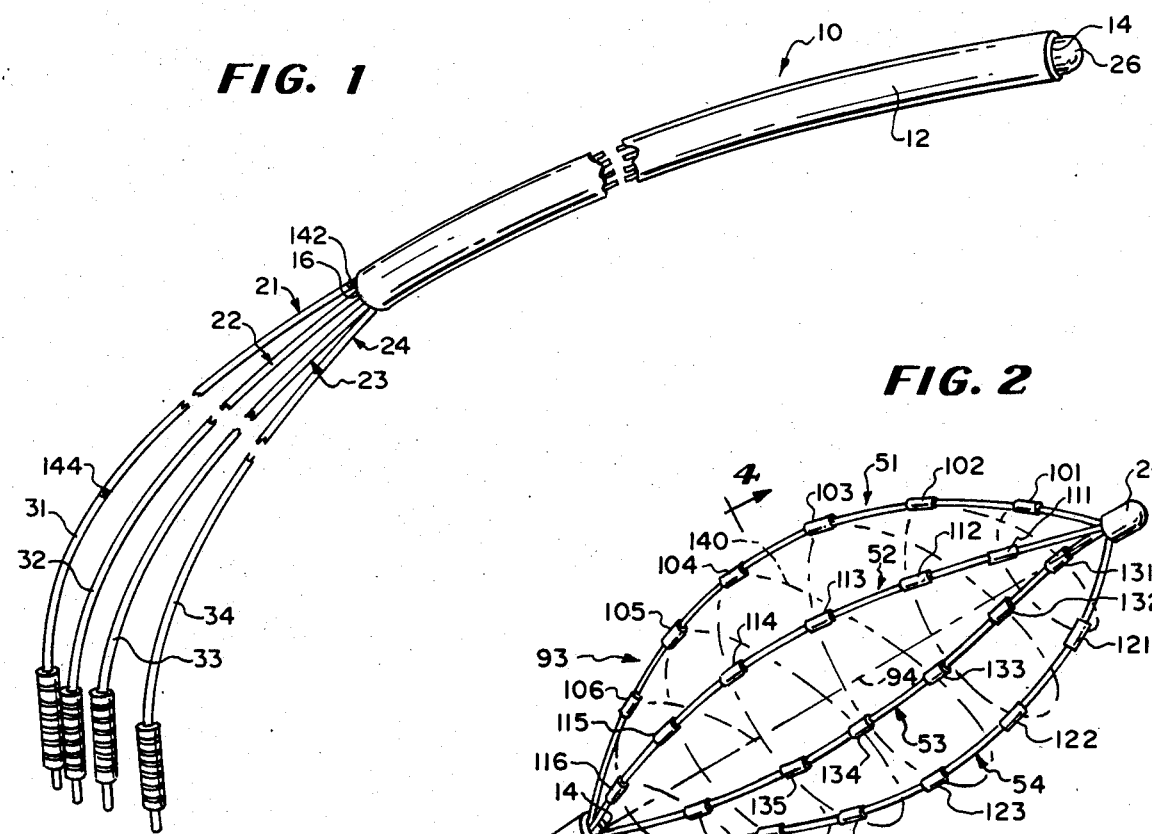

INTRAVENTRICULAR MULTIELECTRODE CARDIAL MAPPING PROBE AND METHOD FOR USING SAME

BACKGROUND OF THE INVENTION

1. Field of the Invention

The present invention relates to an intraventricular multielectrode cardiac mapping probe and to a method of using same for endocardial mapping of a heart chamber, such as a ventricle.

2. Description of the Prior Art

Cardiac mapping is a method by which potentials recorded directly from the heart are spatially depicted as a function of time in an integrated manner. Electrodes are utilized for recording potentials at different positions on the wall surface of a heart chamber, such as the endocardial wall of a ventricle, so that various and important electrophysiological variables can be identified from the cardiac recordings. Such variables include local activation times, waveform analyses, and potential distribution during depolarization and repolarization. Cardiac mapping is very important in locating abnormal foci in the heart and the mapping probe may even be utilized in destroying such foci.

Information on techniques of cardiac mapping are disclosed in numerous articles written about cardiac mapping and one very informative article containing much background information on cardiac mapping is "Techniques of Intraoperative Electrophysiologic Mapping" by John J. Gallagher, et al. which appeared in the January, 1982 issue of "The American Journal of Cardiology", Volume 49, pages 221–240.

Cardiac mapping can be performed in an epicardial manner, that is to say, on the exterior wall surface of the heart, and in an endocardial manner, that is, within an interior chamber wall or endocardial wall in the heart.

Mapping often requires a difficult and risky surgical procedure where an incision is made through the chest wall for epicardial mapping, and further, through the wall of the heart for endocardial mapping so that a sensing probe (or electrode) can be positioned within the heart chamber at different positions on the wall of the heart chamber.

It will be appreciated that this can be an involved and risky procedure, and accordingly, it is desirable to provide an endocardial procedure that does not require cutting through the chest wall and through the heart wall while still being able to make endocardial measurements of different potentials on an interior heart chamber wall for creating a potential distribution map.

Endocardial mapping is preferred since with epicardial mapping it is not certain that epicardial conduction pathway mapping represents "true" conduction pathways. Further, epicardial mapping is a very traumatic procedure.

Accordingly, limited invasive endocardial mapping is preferred and one way of carrying out such mapping has been with multiple electrodes arranged along a single axis on one lead.

A number of devices have been proposed which have multiple electrodes and which can be inserted through a vein or other passageway into a chamber for mapping potentials within the chamber, for sensing and/or for stimulating. Examples of these previous probes and their methods of use are disclosed in the following U.S. Patents:

| U.S. PAT. NO. | PATENTEE |
| --- | --- |
| 3,326,207 | Egan |
| 3,825,015 | Berkovits |
| 3,903,897 | Woollons et al. |
| 3,995,623 | Blake et al. |
| 4,172,451 | Kline |

The Egan U.S. Pat. No. 3,326,207 merely discloses an electrocardiac instrument for testing unborn infants, which instrument includes a balloon on which electrodes are positioned and which can be inserted into the uterus and positioned adjacent a fetus for recording various potentials once the balloon is inflated.

The Berkovits U.S. Pat. No. 3,825,015 discloses a single catheter for atrial and ventricular stimulation where the distal end portion of the catheter has a number of ring electrodes mounted thereon which can be used for sensing potentials within a heart chamber such as in the atrium or in the ventricle.

The Woollons et al U.S. Pat. No. 3,903,897 discloses a cardiac pacer having several ventricular poles or electrodes at a distal end of a pacing lead and several atrial poles spaced a short distance behind the ventricular poles. The atrial poles are, of course, utilized for sensing potentials within the atrium.

The Blake et al U.S. Pat. No. 3,995,623 discloses a multipurpose flow-directed catheter which has a number of ring electrodes thereon for sensing various potentials within a ventricle and within an atrium.

The Kline U.S. Pat. No. 4,172,451 discloses an intracardiac electrode and a method for manufacturing same. The electrode comprises an outer flexible tube containing a plurality of wire leads which extend to perforations in the distal end of a tube forming part of the electrode. The wire lead ends form electrodes which can be utilized for sensing potentials within a heart chamber and particularly for receiving and transmitting electric impulses from different points on a heart wall to a recording and/or information storage unit for direct observation or subsequent analysis.

Except for the balloon structure shown in the Egan U.S. Pat. No. 3,326,207, all of the above referred to patents only disclose elongate, finger-like, lead body distal end portions which have electrodes thereon, and do not provide any form of probe which can be manipulated to form an elliptical envelope whereby electrodes on wire assemblies forming the elliptical envelope can measure various potentials within a heart chamber as provided in the cardiac mapping probe of the present invention.

However, it has been known in the non-analogous art of devices for clearing blood clots to provide an assembly of expandable wires for clearing a blood clot, which expandable wires are inserted into a vein or artery in a generally straight configuration and then are caused to expand outwardly to engage side walls of the vein. Such a non-analogous blood clot filter assembly is disclosed in U.S. Pat. No. 4,425,908.

Also it has been proposed in non-analogous U.S. Pat. No. 4,432,369 to provide an electromagnetic sensor having three electrodes positioned within an elliptical frame which can be inserted in a vein. A generator of a magnetic field is then utilized for measuring signals from the electrodes in this non-analogous electromagnetic sensor, such signals being indicative of a biological condition such as (a) fluid flow in a vein or artery, (b) an esophageal muscular condition or (c) the diameter of a blood vessel.

As will be described in greater detail hereinafter, the intraventricular multielectrode cardiac mapping probe of the present invention differs from the various devices disclosed and described in the patents referred to above by providing at least one, and preferably a plurality, e.g. four, wire assemblies which are movable within a catheter from a position where distal end portions of the wire assemblies are retracted within the catheter and an extended position where the distal end portions of the wire assemblies are extended within a heart chamber and where they are caused to move outwardly to form a generally elliptical envelope so that a plurality of sleeve electrodes, spaced apart on each wire assembly, can contact points on an endocardial wall of a heart chamber, such as an atrium or a ventricle, for making potential measurements at those points. This probe construction provides for electrodes arranged in three dimensions and for a larger number of sensing electrodes than are provided in the prior devices where electrodes are mounted on a single axis.

SUMMARY OF THE INVENTION

According to the invention there is provided an intraventricular multielectrode cardiac mapping probe comprising a catheter having an open proximal end and an open distal end and a lumen confluent with the open proximal and distal ends. A plurality of elongate wire assemblies are slidably received within the lumen of the catheter. The wire assemblies have distal end portions connected to a tip member and proximal end portions extending from the proximal open end of the catheter. Each wire assembly includes a tubing, a central core wire of a preformed configuration received in the tubing and a plurality of insulated wire conductors also received within the tubing and extending substantially the length thereof. A plurality of spaced apart sleeve electrodes are mounted on the distal portion of the tubing with each of the sleeve electrodes being in electrical continuity with one of the conductor wires. Means (such as the proximal ends of the wire assemblies) are provided for advancing the plurality of wire assemblies which are connected to the tip member in the lumen of the catheter from a position where the distal tip member is retracted within the catheter to a position where the distal tip member is extended from the catheter after the catheter has been inserted into an artery or vein placing the distal end opening into a heart chamber where the tip member and connected wire assemblies are advanced from the distal opening of the catheter. Each wire assembly assumes the preformed bowed configuration of the core wire. The wire assemblies then can be rotated to measure and record electrical potentials along the surface of an endocardial wall of a heart chamber contacting the sleeve electrodes.

BRIEF DESCRIPTION OF THE DRAWINGS

FIG. 1 is a perspective view, with portions broken away, of one embodiment on the intraventricular multielectrode cardiac mapping probe of the present invention.

FIG. 2 is a perspective view, similar to the view shown in FIG. 1, of the mapping probe shown in FIG. 1 and shows a distal end portion of four wire assemblies of the probe extended from a distal open end of a catheter of the probe.

FIG. 3 is a radial sectional view of one of the wire assemblies shown in FIG. 2 and is taken along line 3—3 of FIG. 2.

FIG. 4 is a sectional view through the distal end portion of four extended wire assemblies and is taken along line 4—4 of FIG. 2.

DESCRIPTION OF THE PREFERRED EMBODIMENTS

Figure 5:
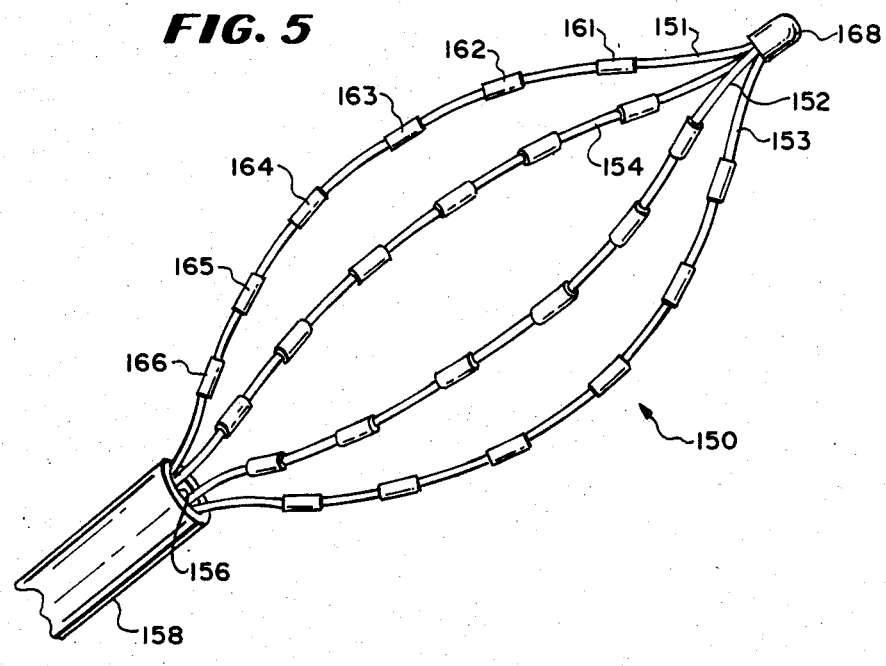
FIG. 5 is a fragmentary perspective view of extended distal end portions of four wire assemblies of another embodiment of the mapping probe of the present invention where the sleeve electrodes on each wire assembly are spaced the same distance from a tip member to which all of the wire assemblies are connected.

Referring now to FIG. 1, there is illustrated therein a perspective view of an intraventricular multielectrode cardiac mapping probe 10 constructed according to the teachings of the invention. As shown, the probe 10 includes an elongate catheter 12 having an open distal end 14 and an open proximal end 16. Situated within the catheter 16 are four wire assemblies 21–24 which are all connected at their distal ends to a tip or cap member 26 that can be made of a conductive metal such as stainless steel and which can have an insulative covering made of polytetrafluroethylene. The catheter 12 can be made of polyurethane or other material which as polytetrafluoroethylene.

Each of the wire assemblies 21–24 has a proximal end portion 31–34 with an excess length or slack portion which extends beyond the open proximal end 16 of the catheter 12. Each proximal end portion 31–34 is connected to a proximal connector 41–44. As will be described in greater detail hereinafter, the wire assemblies 21–24 are slidable or movable within the catheter 12 such that the slack proximal end portions 31–34 can be moved into the catheter 12 so that distal end portions 51–54 (FIG. 2) of the wire assemblies connected to the tip member 26 can be extended from the open distal end 14 of the catheter 10.

The connectors 41–44 can be of any conventional design and will have connector contacts thereon equal to the number of wire conductors included in each wire assembly. In the illustrated embodiment, the connectors 41–44 are generally cylindrical. Also, and as shown in FIG. 3, the wire assembly 21 has six insulated wire conductors 61–66 which are connected to six ring contacts 71–76 on a cylindrical insulating body 78 of the connector 41. The wire assemblies 41–44 are essentially identical at the proximal ends thereof. Also, it will be understood that each assembly has six insulated wire conductors 61–66 therein and that connectors 42–44 are identical in construction to the construction of connector 41 described above.

As best shown in FIG. 3, each wire assembly 21–24 includes a central core wire 79 which is of greater diameter than each of the six insulated wire conductors 61–66 and which is fixed at its distal end, such as by welding, to the tip member 26. The core wire 79 is made of stainless steel, has a diameter of 0.010–0.011 inch and has a sleeve 80 of insulative material thereon. The sleeve 80 is typically made of polytetrafluoroethylene. The wire conductors 61–66 are typically made of 0.003 inch diameter silver and each is surrounded by a sleeve 81–86 of insulative material such as polyurethane or polytetrafluoroethylene.

The six insulated wire conductors 61–66 and the insulated core wire 79 are received within a tubing 90 which can be made of polyurethane or polytetrafluoroethylene.

In the embodiments of the connectors 41–44 shown in FIG. 2, a terminal pin 92 extends from the proximal end of each cylindrical insulating body 78 and is typically defined by the proximal end of the core wire 79.

If it is desired to utilize the core wire 79 as a wire conductor, the tip member 26 can be uninsulated to form an anode and the terminal pin 92 can then serve as an anode connector.

As best shown in FIG. 2, when the proximal end slack portions 31–34 of the wire assemblies 21–24 are moved into the catheter 12, distal end portions 51–54 of the wire assemblies 21–24 extend from the open distal end 14.

To ensure the creation of an elliptical envelope 93, the distal end portion of each core wire 79 has a preformed configuration, typically a bowed configuration, so that it will extend radially outwardly from an axis 94 extending through an elongate axis of the tip member 26 and the catheter 12 as indicated in FIG. 2.

As shown in FIG. 2, the distal end portion 51 has six sleeve electrodes 101–106 thereon, the distal end portion 52 has six sleeve electrodes 111–116 thereon, the distal end portion 53 has six sleeve electrodes 131–136 thereon and the distal end portion 54 has six sleeve electrodes 131–136 thereon. The sleeve electrodes 101, 102, . . . 136 can be made of platinum or stainless steel.

It will be apparent from FIG. 2 that the first sleeve electrode 101 on distal end portion 51 is closer to the tip member 26 than any of the other most distal sleeve electrodes 111, 121, and 131 on the other distal end portions 52, 53 and 54 In this respect, the sleeve electrodes 101–106, 111–116, 121–126 and 131–136 are staggered relative to one another so that when the distal end portions 51–54 are retracted back into the catheter 12, none of the sleeve electrodes 101–106 will contact another sleeve electrode 111–116 and instead will be staggered one behind the other with the sleeve electrode 101 being the most distal sleeve electrode followed by sleeve electrode 111, sleeve electrode 121, sleeve electrode 131, sleeve electrode 102, sleeve electrode 112, etc.

Stated another way, a line drawn about the periphery of the elliptical envelope 92 and extending from the most distal sleeve electrode 101 on the wire assembly distal end portion 51 to the most proximal sleeve electrode 136 on the wire assembly distal end portion 54 will define a generally spiral path as shown by the dashed spiral line 140 in FIG. 2.

Each sleeve electrode 101, 102, 103, 104, 105 and 106 is received over the insulating tubing 90 of the distal end portion 51 and in a position about and covering an opening (not shown) in the tubing 90 where one of the insulated wire conductors 61–66 with insulation removed therefrom extends out from the tubing 90. Such uninsulated end portion is typically coiled around the tubing 90 so that the sleeve 101 . . . or 106 can make a good electrical connection therewith, or is otherwise bonded to one of the sleeve electrodes 101, 102, 103, 104, 105, or 106. Various connections of conductors to sleeves are known in the art and are disclosed, for example, in U.S. Pat. Nos. 3,664,347; 3,769,984; 3,825,015; and 3,942,536. It will be understood that the sleeve electrodes 111–116, 121–126, 131–136 on distal end portions 52–54 are each mounted on a tubing 90 and connected to a wire conductor 62, 63, 64, 65 or 66 in the same manner as the sleeve electrodes 101–106 are mounted and connected on the tubing 90 in the distal end portion 51.

Also it is to be understood that even though the sleeve electrodes 101–106, 111–116, 121–126, 131–136 are shown mounted in a non-isodiametric manner on the tubings 90 of each wire assembly 51–54, such sleeve electrodes 101–106, 111–116, 121–126 and 131–136 can be formed isodiametric with the tubing 90 so as to provide a smooth, continuous peripheral surface on each distal end portion 51–54.

In the use of the cardiac mapping probe 10, the sleeve electrodes 101–106, 111–116, 121–126 and 131–136 and the tip member 26 (if it is utilized as an electrode also) will be positioned within a heart chamber, such as a ventricle, and the electrical potentials at each of the electrodes will be sensed and conducted by the respective wire conductors 61–66 to the respective connectors 41–44 which are received in suitable coded socket connectors so that the position at which an electrode sleeve 101–106, 111–116, 121–126 and 131–136 is located on one of the distal end portions 51–54 can be correlated with the potential sensed by that sleeve electrode 101–106, 111–116, 12–126 or 131–136.

Typically in using the cardiac mapping probe 10, a physician will insert the catheter 12 through the vascular system and into the chamber of the heart to be mapped (an example would be through the aorta, across the aortic valve, through the atrium, and into the left ventricle). When the proper inserted position of the catheter 13 has been determined by fluoroscopy or other means, the distal end portions 51–54 of the wire conductors are extended by pushing the slack proximal end portions 31–34 of the wire assemblies 21–24 into the catheter 12 a predetermined distance. For this purpose, color markings can be provided on the slack portions 31–34 showing the position where the distal end portions 51–54 of the wire assemblies 21–24 are fully retracted and showing the extent to which the slack proximal end portions 51–54 are inserted into the catheter 12 to obtain the desired length of extension of the distal end FIG. 1. In one embodiment of the probe 10, the length of the extended distal end portions 51–54 was 9 cm. and the catheter 12 had a length of 110 cm.

Once the distal end portions 51–54 have been extended the desired distances e.g., 9 cm., the connectors 41–44 are connected in appropriate sockets in a potential sensing and recording apparatus (not shown). Then, all the potentials at the various electrodes are sensed by the apparatus. Next, the wire assemblies 21–24 are rotated a predetrmined arcuate distance. Typically, exact incremental rotational indexing of the elliptical envelope 92 of the wire assembly distal end portions 51–54 is difficult to accomplish, except with the assistance of fluoroscopy or with the use of other imaging systems. Accordingly, the wire assemblies 51–54, instead, may be indexed or rotated ⅛, 1/6, 1/5, ¼ or ⅓ of a revolution of the assemblies 51–54 in the catheter 12 and after each rotational indexing, further potential measurements are made. Then, the wire assemblies 51–54 are indexed again and additional measurements are made until the wire assemblies have been rotated 360°. In this way, potentials are sensed at different positions within the ventricle going along the wall of the ventricle, from the aortic valve to the apex of the ventricle, and generally in circles about the generally elliptical envelope 92 received in the ventricle.

In FIG. 5 is shown another embodiment of a mapping probe 150 of the present invention wherein four distal end portions 151-154 of four wire assemblies, similar to wire assemblies 21-24 shown in FIG. 2 are shown extended from an open distal end 156 of a catheter 150 of the probe 150. Here each distal end portion 151-154 has six sleeve electrodes 161-166 and all the electrodes 161-166 on each distal end portion 151, 152, 153 or 154 are spaced the same distance from a tip member 168 to which each wire assembly 151-154 is connected such that these electrodes 161-166 are not staggered in the manner of the sleeve electrodes 101-106, 111-116, 121-126 and 131-136 shown in FIG. 2.

With this embodiment, once the distal end portions 151-154 have been positioned within the ventricle and potentials at the various sleeve electrodes 161-166 on each distal end portion 151-154 have been sensed and measured, the wire assemblies 151-154 can be rotated in increments until approximately 90° of rotation have been achieved and at that point the sleeve electrodes 161-166 on distal end portion 154 should be at the first position of the sleeve electrodes 161-166 on the distal end portion 151 and this can be confirmed by the potentials sensed and recorded by the sensing and recording apparatus.

With this probe 150, it is not necessary to rotate the probe more than 90°. However, electric potentials are not measured in the area of the envelope between adjacent sleeve electrodes 161, 162; 162, 163; 163, 164; 164, 165; and 165, 166.

Figure 6:
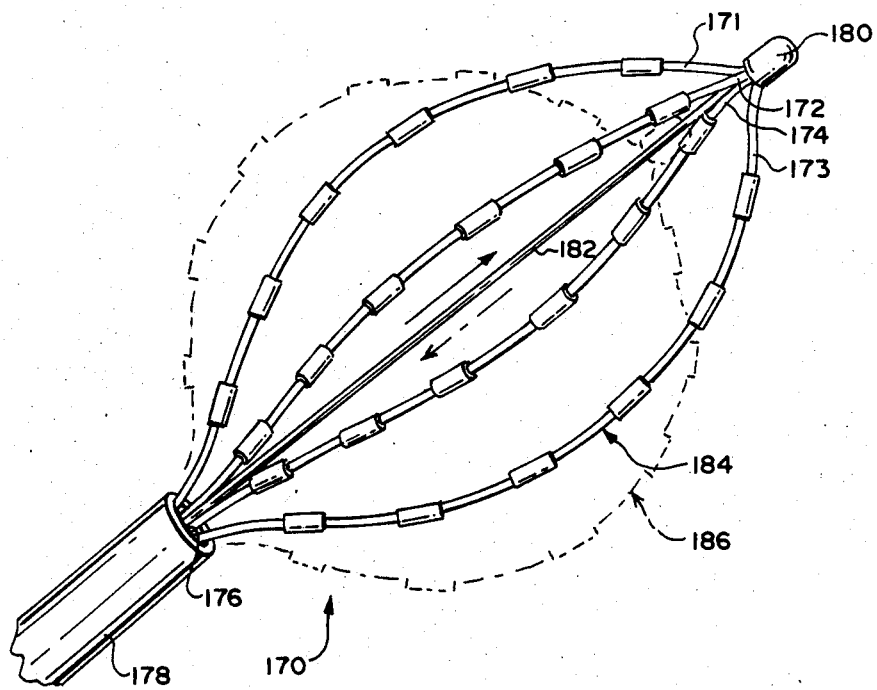
FIG. 6 is a fragementary perspective view of extended distal end portions of four wire assemblies of still another embodiment of the mapping probe of the present invention, shows all wire assemblies connected to a tip member, and shows a central control wire connected to the tip member for expanding or contracting the envelope defined by the extended wire assemblies upon movement of the control wire.

In FIG. 6 is illustrated still a further embodiment of a mapping probe 170 constructed according to the teachings of the present invention. Here four distal end portions 171-174 of four wire assemblies, similar to the distal end portions 151-154 shown in FIG. 6, are shown extended from an open distal end 176 of a catheter 178 of the probe 170 and connected (welded) to a tip or cap member 180 at their distal ends. In addition to the distal end portions 171-174 of the four wire assemblies there is also provided a control wire or rod 182 which is received within the catheter 178 and which extends outwardly and is connected (welded) to the tip member 180. This control wire 182 can be used in the manner of a control rod or stem of an umbrella to increase the maximum diameter of an elliptical envelope 184. In this respect, after the wire assembly distal end portions 171-174 have been extended to create the envelope 184, the control wire 182 can be retracted into the catheter 178 to create a large envelope 186 (shown in phantom) which is larger than the envelope 184. Alternatively, the control wire 182 can be extended to reduce the maximum diameter of the envelope 184 formed by the distal end portions 171-174 of the wire assemblies. While holding the wire assemblies 21-24 extended from the open distal end 14 of the catheter 178 and holding the catheter 178, the control wire 182 can be retracted or extended without dislodging the wire assemblies.

Also, it will be understood that the electrodes 101, 102, . . . , 136 on the wire assemblies 171-174 can be arranged side-by-side, as shown, or in a staggered spiral array in the manner of the arrangement of the electrodes 61-66 shown in FIG. 1.

The various sleeve electrodes 101-106, 111-116, 121-126, 131-136, 161-166 can be used in a unipolar mode where a separate anode connection to the patient's tissue is provided or where the tip member 26, 168, or 180 is used as an anode; or can be used in a bipolar mode where adjacent electrodes are anode and cathode.

The flexing of the extended distal end portions 51-54, 151-154 or 171-174, by reason of the pre-set bowed configuration or by manipulating the control wire 182, allows the sleeve electrodes 101-106, 111-116, 121-126, 131-136, 161-166 to be forced gently against the endocardium assuring good electrical contact with the endocardial wall with minimal trauma, while the loading or carrying of the wire assembly distal end portions 51-54, 151-154 or 171-174 in the catheter 12, 158 or 178 allows for smooth pervenous insertion of the probe 10, 150 or 170 with minimum trauma to the patient. Also, the large number of sleeve electrodes, at least 24 in number, provides for higher resolution and for the obtaining of better data.

Further, if during the mapping procedure an abnormal focus is found (one where the rate is more rapid than those foci found more proximal to the atrial focus and one which would govern the overall heart rate) it can be interrupted or destroyed such as by utilizing a conductive path between two of the sleeve electrodes, to provide a more normal heart rate.

From the foregoing description, it will be apparent that the intraventricular multielectrode cardiac mapping probes 10, 150 and 170 of the present invention have a number of advantages, some of which have been described above and others of which are inherent in the invention. Also, modifications can be made to the mapping probes 10, 150 and 170 without departing from the teachings of the present invention. Accordingly, the scope of the invention is only to be limited as necessitated by the accompanying claims.

We claim:

1. An intraventricular multielectrode cardiac mapping probe comprising a catheter having an open proximal end, an open distal end, and a lumen confluent with said open proximal end and said open distal end; a plurality of elongate wire assemblies slidably received in and movable within said lumen of said catheter; a tip member; each of said wire assemblies having a distal end portion connected to said tip member and a proximal end portion extending from said catheter proximal open end; each of said wire assemblies comprising a tubing, a central core wire having a preformed configuration received in said tubing and a plurality of insulated wire conductors received within said tubing and extending substantially the length thereof; a proximal connector assembly being mounted on each tubing in said proximal end portion of each wire assembly and having electrical contacts thereon connected to respective ones of said wire conductors; and a plurality of spaced apart sleeve electrodes being mounted on each tubing in said distal end portion thereof; each of said sleeve electrodes being in electrical continuity with one of said wire conductors; means for moving said plurality of wire assemblies connected to said tip member in said lumen of said catheter from a position where said distal tip member is retracted within said catheter to a position where said distal tip member is extended from said catheter; said catheter being insertable into an artery or vein to place said distal end opening thereof in a heart chamber where said tip member and said connected wire assemblies are advanced from said distal end opening of said catheter with each said wire assembly assuming said performed configuration of said core wire and said wire assemblies are rotatable to permit measuring and recording of electrical potentials at different points along the surface of an endocardial wall of a heart chamber contacting said sleeve electrodes.

2. The probe of claim 1 wherein each core wire has an insulative covering.

3. The probe of claim 1 wherein said plurality of wire assemblies includes four wire assemblies and said tip member is connected to the distal end of each core wire of each wire assembly.

4. The probe of claim 1 wherein said tip member is an electrode of the multielectrode cardiac mapping probe.

5. The probe of claim 1 wherein each proximal connector is cylindrical in shape and has a proximal pin contact and a plurality of ring contacts.

6. The probe of claim 5 wherein said pin contact is the proximal uninsulated end of said core wire.

7. The probe of claim 5 wherein said pin contact is connected to the proximal uninsulated end of said core wire.

8. The probe of claim 1 wherein each wire assembly comprises six insulated wire conductors and said tubing in said distal end portion of said wire assembly has six of said sleeve electrodes mounted thereon in a spaced apart array, each sleeve electrode being connected to one of said wire conductors.

9. The probe of claim 8 wherein each of said core wires has a bowed configuration defining said desired configuration such that, when said wire assemblies are extended, they define together a generally elliptical envelope.

10. The probe of claim 8 wherein said sleeve electrodes on each wire assembly are staggered relative to the sleeve electrodes on adjacent wire assemblies such that, when the wire assemblies are extended, a spiral path is established around the assemblies extending from the most distal sleeve electrode on a first wire assembly to the most proximal electrode on a fourth wire assembly.

11. The probe of claim 10 wherein the length of each sleeve electrode and said staggerd arrangement are such that sleeve electrode overlaps other sleeve electrodes when the wire assemblies are retracted within said catheter.

12. The probe of claim 8 wherein said sleeve electrodes on each wire assembly are all spaced equal distances from each other and the most distal sleeve electrode on each wire assembly is spaced the same distance from said cap member as the other distal sleeve electrodes on the other wire assemblies so that six circular paths are established for each aligned, side-by-side group of four electrodes on the four wire assemblies.

13. The probe of claim 8 including a stiff but flexible control wire having a distal end connected to said tip member and an elongate body slidably received adjacent to but not connected to said wire assemblies in said catheter, a proximal end of said control wire extending from said open proximal end of said catheter, and means for moving said control wire relative to said wire assemblies and said catheter, whereby, after said distal end portions of said wire assemblies are extended to form an envelope, said control wire can be moved axially of said catheter to extend said wire assemblies radially outwardly or to pull said wire assemblies radially inwardly to change the shape defined by the assemblies, each said core wire defining means for causing said wire assemblies to assume a desired bowed configuration.

14. The probe of claim 1 wherein said preformed configuration of said core wire of wire assembly distal end portion is a bowed configuration.

15. The probe of claim 1 wherein each uninsulated wire conductor distal end extends out of said tubing and is coiled around said tubing beneath an adjacent sleeve electrode for making electrical contact with same.

16. The probe of claim 15 wherein said coiled end portion of each wire conductor is bonded to the underside of one of said sleeve electrodes.

17. A method for cardiac mapping of the endocardial wall of a heart chamber, such as a ventricle, using a probe comprising a catheter having a lumen and open proximal and distal ends, a plurality of elongate wire assemblies slidably received within said lumen of said catheter; a tip member connecting the distal ends of said wire assemblies together, the distal end portion of each wire assembly having a preformed configuration, each wire assembly including a tubing and a plurality of wire conductors in said tubing, a plurality of spaced apart sleeve electrodes mounted on the distal end portion of said tubing in electrical continuity with respective ones of said wire conductors, and proximal connector contacts at the proximal end of said tubing in electrical continuity with respective ones of said wire conductors, said method including the steps of: inserting the probe through an artery or vein into a heart chamber; extending said distal end portions of said plurality of wire assemblies a desired distance from said catheter open distal end; causing said wire assemblies to assume the preformed configuration where said sleeve electrodes contact the endocardial wall of the heart chamber; connecting said proximal connector contacts to means for sensing and recording electrical potentials; measuring and recording the electrical potentials at the points where said sleeve electrodes are in contact with the endocardial wall; rotating said wire assemblies within said heart chamber a predetermined peripheral incremental distance about said envelope; repeating the measuring and recording step; and repeating the rotating step and the measuring and recording step as necessary until the wire assemblies have been rotated through a desired angle.

18. A method for cardiac mapping the endocardial wall of a heart chamber, such as a ventricle, using a multielectrode probe comprising a catheter having a lumen and open proximal and distal ends, four elongate wire assemblies slidably received within said lumen of said catheter; a tip member connecting the distal ends of said wire assemblies together, the distal end portion of each wire assembly having a preformed configuration, each wire assembly including a tubing and six wire conductors in said tubing, six spaced apart sleeve electrodes mounted on said distal end portion of said tubing in electrical continuity with respective ones of said wire conductors, and six proximal connector contacts at the proximal end of said tubing in electrical continuity with respective ones of said wire conductors, said method including the steps of: inserting the probe through an artery or vein into a heart chamber; extending said distal end portion of each wire assembly a desired from said catheter open distal end; causing each core wire to assume the preformed configuration where said sleeve electrodes contact the endocardial wall of the heart chamber; connecting said proximal connector contacts to means for sensing and recording electric potentials;

measuring and recording the electric potentials at the points where said sleeve electrodes are in contact with the endocardial wall; rotating said probe within said heart chamber a predetermined peripheral incremental distance about said envelope; repeating the measuring and recording step; and repeating the rotating step and the measuring and recording step as necessary until the wire assemblies have been rotated through a desired angle.

19. A method for cardiac mapping the endocardial wall of a heart chamber, such as a ventricle, using a multielectrode probe comprising a catheter having a lumen and open proximal and distal ends, four elongate wire assemlbies slidably received within said lumen of said catheter; a tip member connecting the distal ends of said wire assemblies together, the distal end portion of each wire assembly having a preformed configuration each wire assembly including a tubing and six wire conductors in said tubing, six spaced apart sleeve electrodes mounted in a staggered manner on said distal end portion of said tubing in electrical continuity with respective ones of said wire conductors, and six proximal connector contacts at the proximal end of said tubing in electrical continuity with respective ones of said wire conductors, said method including the steps of: inserting the probe through an artery or vein into a heart chamber; extending said distal end portion of each wire assembly a desired distance from said catheter open distal end; causing each core wire to assume the desired configuration where said sleeve electrodes contact the endocardial wall of the heart chamber; connecting said proximal connector contacts to means for sensing and recording electric potentials; measuring and recording the electric portentials at the points where said sleeve electrodes are in contact with the endocardial wall; rotating said wire assemblies within said heart chamber a predetermined peripheral incremental distance about said envelope; repeating the measuring and recording step; and repeating the rotating step and the measuring and recording step as necessary until the wire assemblies have been rotated through a desired angle.

20. A method for cardiac mapping the endocardial wall of a heart chamber, such as a ventricle, using a multielectrode probe comprising a catheter having a lumen and open proximal and distal ends, four elongate wire assemblies slidably received within said lumen of said catheter; a tip member connecting the distal ends of said wire assemblies together, the distal end portion of each wire assembly having a preformed configuration each wire assembly including a tubing and six wire conductors in said tubing, six spaced apart sleeve electrodes mounted on said distal end portion of said tubing and positioned an equal distance from each other with each sleeve electrode being adjacent to a sleeve electrode on a proximate wire assembly and being in electrical continuity with respective ones of said wire conductors, and six proximal connector contacts at the proximal end of said tubing in electrical continuity with respective ones of said wire conductors, said method including the steps of: inserting the probe through an artery or vein into a heart chamber; extending said disal end portion of each wire assembly a desired distance from said catheter open distal end; causing each core wire to assume the desired configuration where said sleeve electrodes contact the endocardial wall of the heart chamber; connecting said proximal connector contacts to means for sensing and recording potentials; measuring and recording the electric potentials at the points where said sleeve electrodes are in contact with the endocardial wall; rotating said wire assemblies within said heart chamber a predetermined peripheral incremental distance about said envelope; repeating the measuring and recording step; and repeating the rotating step and the measuring and recording step until the wire assemblies have been rotated through a desired angle.

21. A method for cardiac mapping the endocardial wall of a heart chamber, such as a ventricle, using a multielectrode probe comprising a catheter having a lumen and open proximal and distal ends, a plurality of elongate wire assemblies slidably received within said lumen of said catheter; a tip member connecting the distal ends of said wire assemblies together, the distal end portion of each wire assembly having a preformed configuration each wire assembly including a tubing and a plurality of wire conductors in said tubing, a plurality of spaced apart sleeve electrodes mounted on said distal end portion of said tubing in electrical continuity with respective ones of said wire conductors, proximal connector contacts at the proximal end of said tubing in electrical continuity with respective ones of said wire conductors, a flexible control wire connected to the joined distal ends of said wire assemblies and said control wire extending from said distal end to exit the proximal end of said catheter, said method including the steps of: inserting the probe through an artery or vein into the heart chamber; extending said distal end portion of each wire assemblies a desired distance from said catheter open distal end into the heart chamber; manipulating said control rod to cause each core wire to assume the desired configuration where said sleeve electrodes contact the endocardial wall of the heart chamber; connecting said proximal connector contacts to means for sensing and recording electric potentials; measuring and recording the electric potentials at the points where said sleeve electrodes are in contact with the endocardial wall; rotating said wire assemblies within said heart chamber a predetermined peripheral incremental distance about said envelope; repeating the measuring and recording step; and repeating the rotating step and the measuring and recording step as necessary until the wire assemblies have been rotated through a desired angle.

22. An intraventricular multielectrode cardiac mapping probe comprising: a catheter having an open proximal end and an open distal end, four elongate wire assemblies slidably received in said catheter, each wire assembly having a proximal and portion extending from said catheter proximal open end and a distal end portion which is moved in and out of said open distal end of said catheter, each wire assembly comprising a tubing, a central core wire which is stiff but yet flexible and which is received in said tubing and six insulated wire conductors within said tubing extending substantially the entire length thereof, the proximal end of each wire assembly having a proximal connector assembly mounted thereon with each proximal connector assembly having six electrical contacts thereon connected to respective ones of said wire conductors, and the distal end portion of each tubing having six spaced apart sleeve electrodes thereon, each wire conductor being in electrical continuity with one of said sleeve electrodes, said sleeve electrodes on each wire assembly being staggered relative to the sleeve electrodes on adjacent wire assemblies such that, when the wire assemblies are extended, a spiral path is established around the assemblies extending from the most distal sleeve electrode on a first wire assembly to the most proximal sleeve electrode on a fourth wire assembly, the portion of each core wire in each distal end portion of each wire assembly being formed with a predetermined bowed configuration, and a tip member, the distal end of each core wire being connected to said tip member, whereby, when said wire assembly distal end portions are retracted into said catheter, they are squeeezed together within said catheter and, when said wire assembly distal end portions are extended from said catheter by pushing said proximal end portions of said wire assemblies into said open proximal end of said catheter, each wire assembly distal end portion will assume the desired bowed configuration so as to form an elliptical envelope which can make contact with the interior wall surface of a heart chamber.

23. An intraventricular multielectrode cardiac mapping probe comprising: a catheter having an open proximal end and an open distal end, four elongate wire assemblies slidably received in said catheter, each wire assembly having a proximal end portion extending from said catheter proximal open end and a distal end portion which is moved in and out of said open distal end of said catheter, each wire assembly comprising a tubing, a central core wire which is stiff but yet flexible and which is received in said tubing and six insulated wire conductors within said tubing extending substantially the entire length thereof, the proximal end of each wire assembly having a proximal connector assembly mounted thereon with each proximal connector assembly having six electrical contacts thereon connected to respective ones of said wire conductors, and the distal end portion of each tubing having six spaced apart sleeve electrodes thereon, each sleeve electrode being in electrical continuity with one of said wire conductors, and a cap member, the distal end of each core wire being connected to said cap member, said sleeve electrodes on each wire assembly being spaced the same distances from each other and the most distal sleeve electrode on each wire assembly being spaced the same distance from said cap member as the other distal sleeve electrodes on the other wire assemblies so that six circular paths are established for each aligned, side-by-side group of four electrodes on the respective four wire assemblies, the portion of each core wire in each distal end portion of each wire assembly being formed with a predetermined bowed configuration, whereby, when said wire assembly distal end portions are retracted into said catheter, they are squeezed together within said catheter and, when said wire assembly distal end portions are extended from said catheter by pushing said proximal end of said catheter, each wire assembly distal end portion will assume the desired bowed configuration so as to form an elliptical envelope which can make contact with the interior wall surface of a heart chamber.

24. An intraventricular multielectrode cardiac mapping probe comprising: a catheter having an open proximal end and an open distal end, four elongate wire assemblies slidably received in said catheter, each wire assembly having a proximal end portion extending from said catheter proximal open end and a distal end portion which is moved in and out of said open distal end of said catheter, each wire assembly comprising a tubing, a central core wire which is stiff but yet flexible and which is received in said tubing and six insulated wire conductors within said tubing extending substantially the entire length thereof, the proximal end of each wire assembly having a proximal connector assembly having six electric contacts thereon connected to respective ones of said wire conductors, and said distal end portions of each tubing having six spaced apart sleeve electrodes thereon, each of said sleeve electrodes being connected to one of said wire conductors, said sleeve electrodes on each wire assembly being staggered relative to the sleeve electrodes on adjacent wire assemblies such that, when the wire assemblies are extended, a spiral path is established around the assemblies extending from the most distal sleeve electrode on a first wire assembly to the most proximal electrode on a fourth wire assembly, a tip member, the distal end of each core wire being connected to said tip member, and a control rod in each wire assembly having a manipulatable proximal end extending from said catheter open proximal end and a distal end connected to said tip member whereby, when said wire assembly distal end portions are retracted into said catheter, they are squeezed together with said control wire within said catheter and whereby, after said wire assembly distal end portions are extended from said catheter by pushing said proximal end portions of said wire assemblies into said open proximal end of said catheter, said control rod can be moved inwardly or outwardly to cause each wire assembly distal end portion to assume a desired bowed configuration so as to form an elliptical envelope which makes contact with the interior wall of a heart chamber.

25. An intraventricular multielectrode cardiac mapping probe comprising: a catheter having an open proximal end and an open distal end, four elongate wire assemblies slidably received in said catheter, each wire assembly having a proximal end portion extending from said catheter proximal open end and a distal end portion which is moved in and out of said open distal end of said catheter, each wire assembly comprising a tubing, a central core wire which is stiff but yet flexible and which is received in said tubing and six insulated wire conductors within said tubing extending substantially the entire length thereof, the proximal end of each wire assembly having a proximal connector assembly mounted thereon with each proximal connector assembly having six electrical contacts thereon connected to respective ones of said wire conductors, and said distal end portion of each tubing having six spaced apart sleeve electrodes thereon, each sleeve electrode being in electrical continuity with one of said conductors, a cap member, the distal end of each core wire being connected to said cap member, said sleeve electrodes on each wire assembly being spaced the same distances from each other and the most distal sleeve electrode on each wire assembly is spaced the same distance from said cap member as the other distal sleeve electrodes on the other wire assembly so that six circular paths are established for each aligned, side-by-side group of four electrodes on the respective four wire assemblies, and a control rod in each wire assembly having a manipulatable proximal end extending from said catheter open proximal end and a distal end connected to said cap member whereby, when said wire assembly distal end portions are retracted into said catheter, they are squeezed together with said control wire within said catheter and whereby, after said wire assembly distal end portions are extended from said catheter by pushing said proximal end portions of said wire assemblies into said proximal end of said catheter, said control rod can be moved inwardly or outwardly to cause each wire assembly distal end portion to assume a desired bowed configuration so as to form an elliptical envelope which makes contact with the interior wall surface of a heart chamber.

* * * * *

UNITED STATES PATENT AND TRADEMARK OFFICE
CERTIFICATE OF CORRECTION

PATENT NO. : 4,699,147

DATED : October 13, 1987

INVENTOR(S) : Donald A. Chilson and Kevin W. Smith

It is certified that error appears in the above-identified patent and that said Letters Patent is hereby corrected as shown below:

On the title page item [54] should read as follows:

--[54] INTRAVENTRICULAR MULTIELECTRODE CARDIAC MAPPING PROBE AND METHOD FOR USING SAME-- and, item [73] should read as follows:

--[73] Assignee: Cordis Corporation, Miami, Fla. part interest.

Signed and Sealed this

Thirtieth Day of April, 1991

Attest:

HARRY F. MANBECK, JR.

Attesting Officer

Commissioner of Patents and Trademarks